(12) United States Patent
Kazato et al.

(10) Patent No.: US 6,728,405 B1
(45) Date of Patent: Apr. 27, 2004

(54) PARTICLE RECOGNITION DEVICE

(75) Inventors: Hirohiko Kazato, Tokyo (JP); Tomoki Hosoi, Tokyo (JP)

(73) Assignee: Yamatake Corporation, Tokyo (JP)

( * ) Notice: Subject to any disclaimer, the term of this patent is extended or adjusted under 35 U.S.C. 154(b) by 0 days.

(21) Appl. No.: 09/601,181

(22) PCT Filed: Nov. 30, 1998

(86) PCT No.: PCT/JP98/05380
§ 371 (c)(1),
(2), (4) Date: Jul. 25, 2000

(87) PCT Pub. No.: WO00/33251
PCT Pub. Date: Jun. 8, 2000

(51) Int. Cl.$^7$ ................................. G06K 9/46
(52) U.S. Cl. ........................................ 382/190
(58) Field of Search .................. 382/109, 110, 382/173, 181, 190, 203, 276; 502/243, 251, 341

(56) References Cited

U.S. PATENT DOCUMENTS 5,715,182 A * 2/1998 Asai et al. ................... 702/22
5,768,412 A * 6/1998 Mitsuyama et al. ........ 382/173

FOREIGN PATENT DOCUMENTS

JP 62-211783 9/1987
JP 6-187437 6/1994

* cited by examiner

Primary Examiner—Daniel Mariam
(74) Attorney, Agent, or Firm—Blakely, Sokoloff, Taylor & Zafman (57) ABSTRACT

An image input section 1 obtains a halftone image IG of a to-be-measured particle group. A binarization section 2 binarizes the halftone image IT to obtain a binary image IB. A distance transform section 3 performs distance transform for the binary image IB to obtain a distance-transformed image ID. In this case, the particle nucleus extraction section 4 obtains particle nucleus candidates from the distance-transformed image ID and extracts a particle nucleus on the basis of the distance between the particle nucleus candidates and a separation parameter PS to obtain a particle nucleus image IC. A particle expansion section 5 performs particle expansion processing for the particle nucleus image IC and distance-transformed image ID to obtain a particle-separated image IS. In this case, the particle expansion section 5 performs particle expansion processing for the particle nucleus in the particle nucleus image IC along the value of distance transform to obtain the particle-separated image IS. A particle is recognized from the particle-separated image IS. In this way, a particle is recognized at a high speed and high accuracy.

14 Claims, 10 Drawing Sheets

FIG. 1

FIG. 2A IB: BINARY IMAGE

FIG. 2B ID: DISTANCE-TRANSFORMED IMAGE

FIG. 2C IC: PARTICLE NUCLEUS IMAGE

FIG. 2D IS: PARTICLE-SEPARATED IMAGE

PARTICLE IMAGE

FIG. 5B

PARTICLE SEPARATION RESULT
( PRIOR ART 1 )

FIG. 5C

PARTICLE SEPARATION RESULT
( PRIOR ART 2 )

FIG. 5D

PARTICLE SEPARATION RESULT
( PRESENT INVENTION )

| METHOD | PROCESSING TIME FOR 100 CYCLES [SEC] | AVERAGE PROCESSING TIME [SEC/CYCLE] |
|---|---|---|
| PRIOR ART 1 | 55 | 0.55 |
| PRIOR ART 2 | 2875 | 28.8 |
| PRESENT INVENTION | 1156 | 11.6 |

PROCESSING TIMES OF RESPECTIVE METHODS ( SPHERICAL PARTICLES )

PARTICLE IMAGE

FIG. 7B

PARTICLE SEPARATION RESULT
( PRIOR ART 1 )

FIG. 7C

PARTICLE SEPARATION RESULT
( PRIOR ART 2 )

FIG. 7D

PARTICLE SEPARATION RESULT
( PRESENT INVENTION )

| METHOD | PROCESSING TIME FOR 100 CYCLES [SEC] | AVERAGE PROCESSING TIME [SEC/CYCLE] |
|---|---|---|
| PRIOR ART 1 | 85 | 0.85 |
| PRIOR ART 2 | 2992 | 29.9 |
| PRESENT INVENTION | 1340 | 13.4 |

PROCESSING TIMES OF RESPECTIVE METHODS ( FERTILIZER )

PARTICLE RECOGNITION DEVICE

1. TECHNICAL FIELD

The present invention relates to a particle recognition apparatus for separating a particle from a halftone image of a to-be-measured particle group represented by a fertilizer, exploded splinters, or vegetables or fruits and recognizing the particle of an element and, more particularly, to a particle recognition apparatus used to measure a particle size distribution or analyze the shape of a pore in a metal, mineral, or fiber.

2. BACKGROUND ART

As particle recognition apparatuses of this type, conventionally, there are particle recognition apparatuses using labeling or particle recognition apparatuses using distance transform.

[Particle Recognition Apparatus Using Labeling (Prior Art 1)]

A particle recognition apparatus using labeling recognizes a particle with the following procedures.

Figures 11A, 11B:
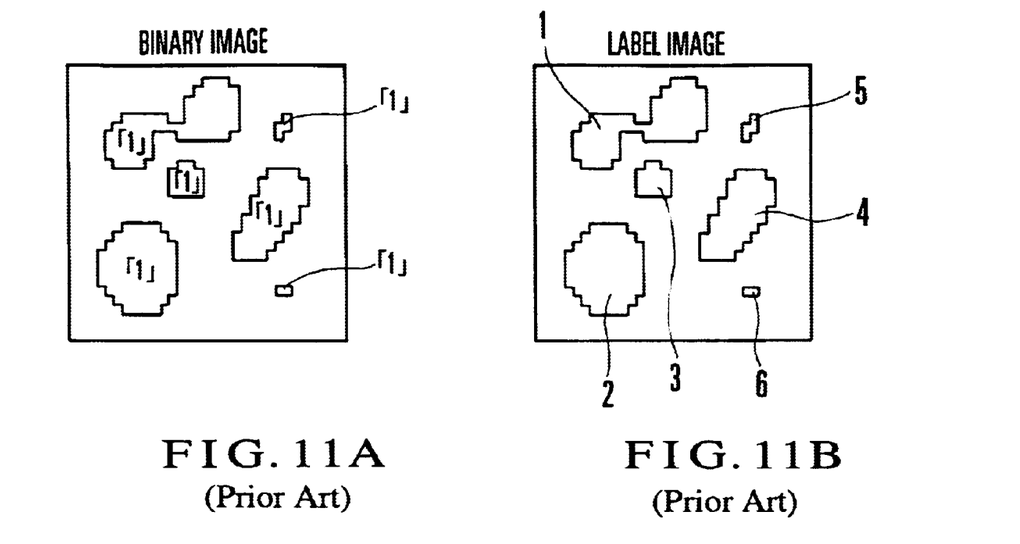
FIG. 11(a) is a view showing a binary image in the particle recognition process by a particle recognition apparatus (prior art 1) using labeling.
FIG. 11(b) is a view showing a label image as the particle recognition result.

(1): A particle group to be measured is photographed to obtain a halftone image.
(2): The halftone image obtained in (1) is binarized ("0", "1") to obtain a binary image (FIG. 11(a)).
(3): The binary image obtained in (2) is labeled to obtain a label image (FIG. 11(b)).
(4): Each label (① to ⑥) is recognized as one particle.

[Particle Recognition Apparatus Using Distance Transform (Prior Art 2)]

A particle recognition apparatus using distance transform recognizes a particle with the following procedures.

Figures 12A, 12B:
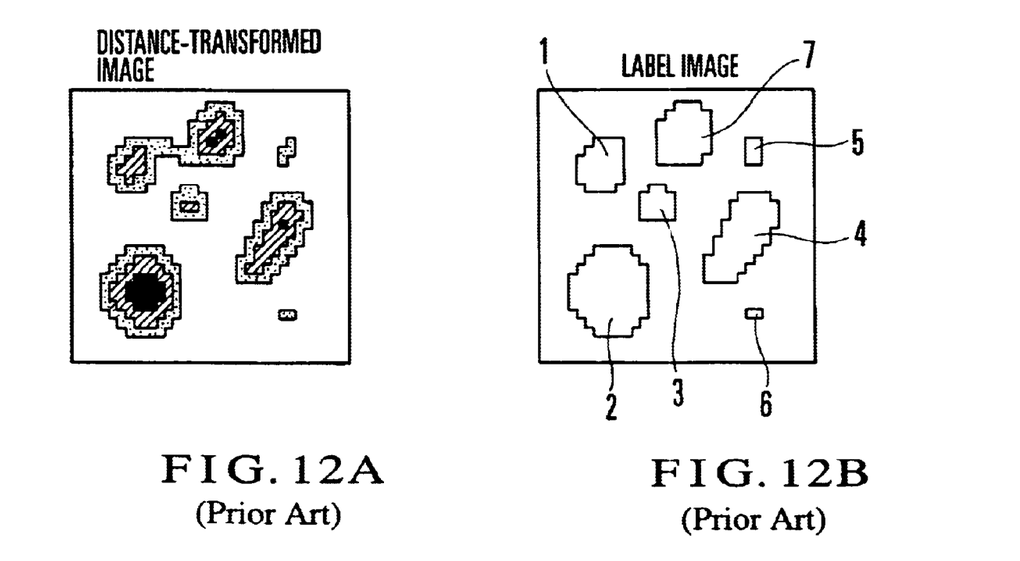
FIG. 12(a) is a view showing a binary image in the particle recognition process by a particle recognition apparatus (prior art 1) using distance transform.
FIG. 12(b) is a view showing a label image as the particle recognition result.
Figure 13A:
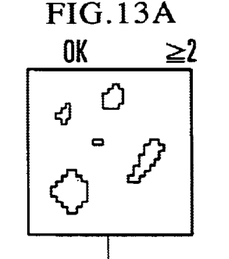
FIG. 13 is a view for explaining the particle recognition process in the particle recognition apparatus (prior art 2) using distance transform.
Figure 13B:
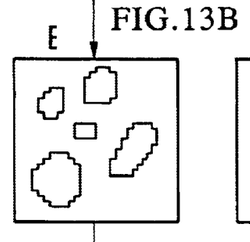
Figures 13C, 13D, 13E, 13F:
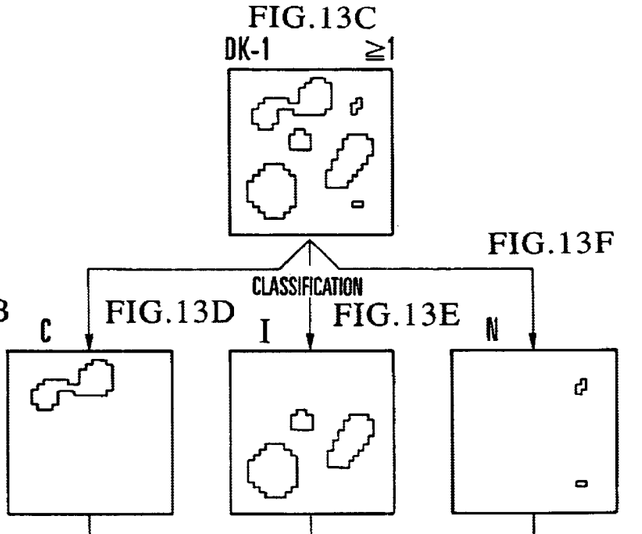
Figure 13G:
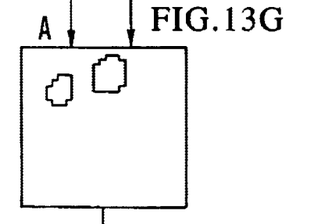
Figure 13H:
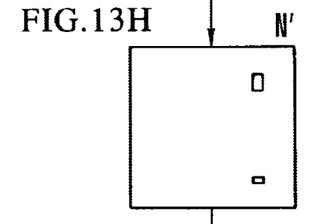
Figure 13I:
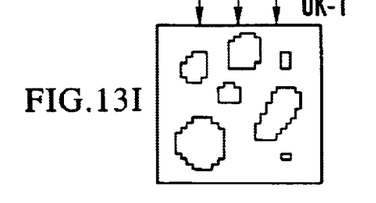

(1): A particle group to be measured is photographed to obtain a halftone image.
(2): The halftone image obtained in (1) is binarized ("0", "1") to obtain a binary image.
(3): The binary image obtained in (2) is subjected to distance transform to obtain a distance-transformed image (FIG. 12(a)).
(4): An image Dk obtained by extracting pixels with values equal to or larger than a threshold value k from the distance-transformed image obtained in (3) to obtain a resultant image line Ok (FIG. 13(a)).
(5): The resultant image line Ok obtained in (4) is subjected to exclusive expansion to obtain an image E (FIG. 13(b)).
(6): A cuttable image C (FIG. 13(d)), uncuttable image I (FIG. 13(e)), and new image N (FIG. 13(f)) are classified from an image $D_{k-1}$ (FIG. 13(c)).
(7): The image C and image E are ANDed to obtain an image A (FIG. 13(g)).
(8): The image N is smoothed to obtain an image N' (FIG. 13(h)).
(9): The image A, image I, and image N' are ORed to obtain an image $O_{k-1}$ (FIG. 13(i)).
(10): Steps (5) to (9) are repeated while decrementing the value k to 1, thereby obtaining a particle-separated image.
(11): The particle-separated image obtained in (10) is labeled to obtain a label image (FIG. 12(b)).
(12):: Each label (① to ⑦) is recognized as one particle.

Note that the particle recognition technique using distance transform is disclosed in, e.g., Japanese Patent Laid-Open No. 62-211783 (image processing apparatus).

3. DISCLOSURE OF INVENTION

Problem to be Solved by the Invention

However, according to such a conventional particle recognition apparatus, in the particle recognition apparatus (prior art 1) using labeling, if a plurality of particles in contact with each other are binarized into the binary image, the plurality of particles in contact are recognized as one particle, resulting in low particle recognition accuracy.

More specifically, in particle recognition using an image, generally, the halftone image of particles is often unclear because of the particle photographing environment, Additionally, in the binary image obtained by binarization, a plurality of particles are often binarized in contact with each other. However, the particle recognition apparatus using labeling often recognizes particles in contact with each other as one particle. This often affects the particle recognition result.

If the binarization level is raised to avoid this problem, particles may be recognized as particles with much smaller sizes, or small particles may disappear.

On the other hand, in the particle recognition apparatus (prior art 2) using distance transform, even when a plurality of particles are binarized into a binary image in contact with each other, they can be recognized as the plurality of particles, respectively. This allows accurate particle recognition. However, since this apparatus uses exclusive expansion processing in separating particles, a phenomenon occurs in which the shape of a separated particle becomes different from the original particle shape. Hence, it is difficult to use this apparatus for the application purpose such as pore shape analysis of a metal or mineral. In addition, this apparatus must repeatedly perform not only calculation for distance transform but also calculation for degeneration for image separation, labeling, exclusive expansion, OR, and AND a plurality of number of times, and the calculation amount is enormous. This takes a long processing time, so this apparatus can be introduced only in an environment with a lenient time limitation.

In a chemical plant for a fertilizer or chemical material, the particle size distribution of a particle group being carried on a belt is measured, and the particle size distribution measurement result is used as feedback information to control the charging amount of a material or water. For this purpose, the particle recognition result must be quickly obtained, and the processing time of particle size distribution measurement is also required to be shorter. In a chemical plant for a fertilizer or chemical material, the processing time taken for particle size distribution measurement must be several sec or shorter. Because of the problem of accuracy, prior art 1 is difficult to use. Prior art 2 cannot be used because it takes several min for particle size distribution measurement due to the enormous calculation amount.

Means of Solution to the Problem

The present invention has been made to solve the above problem, and has as its object to provide a particle recognition apparatus capable of recognizing a particle at a high speed and high accuracy.

In order to achieve the above object, the first invention comprises image input means (1) for obtaining a halftone image (IG) of a particle group to be measured, binarization means (2) for binarizing the halftone image (IG) obtained by the image input means(1) to obtain a binary image (IB), distance transform means (3) for performing distance transform for the binary image (IB) binarized by the binarization means (2) to obtain a distance-transformed image (ID), particle nucleus extraction means (4) for performing particle nucleus extraction processing for the distance-transformed image (ID) obtained by the distance transform means (3) to obtain a particle nucleus image (IC), and particle expansion means (5) for performing particle expansion processing for the particle nucleus image (IC) obtained by the particle nucleus extraction means (4) and the distance-transformed image (ID) obtained by the distance transform means (3) to obtain a particle-separated image (IS).

According to this invention, the halftone image (IG) of the particle group to be measured is binarized into the binary image (IB), the binary image (IB) is subjected to distance transform to obtain the distance-transformed image (ID), and the distance-transformed image (ID) is subjected to particle nucleus extraction processing to obtain the particle nucleus image (IC), and the particle nucleus image (IC) and distance-transformed image (ID) are subjected to particle expansion processing to obtain the particle-separated image (IS).

According to the second invention, in the first invention, particle nucleus candidates are obtained from the distance-transformed image (ID), and a particle nucleus is extracted on the basis of the distance between the particle nucleus candidates.

According to this invention, the particle nucleus candidates are obtained from the distance-transformed image (ID), the particle nucleus is extracted on the basis of the distance between the particle nucleus candidates to obtain the particle nucleus image (IC), and the particle nucleus image (IC) and distance-transformed image (ID) are subjected to particle expansion processing to obtain the particle-separated image (IS).

According to the third invention, in the first invention, parameter setting means for setting a separation parameter (PS) that defines a degree of extraction of the particle nucleus in the particle nucleus extraction processing is provided, and particle nucleus candidates are obtained from the distance-transformed image (ID), and a particle nucleus is extracted on the basis of the distance between the particle nucleus candidates and the separation parameter (PS).

According to this invention, the particle nucleus is extracted on the basis of the distance between the particle nucleus candidates and separation parameter (PS) to obtain the particle nucleus image (IC), and the particle nucleus image (IC) and distance-transformed image (ID) are subjected to particle expansion processing to obtain the particle-separated image (IS). In this case, the degree of extraction of the particle nuclei (the degree of separation of particles) can be adjusted by changing the separation parameter (PS).

According to the fourth invention, in the second invention, a first intermediate image (IT1) is obtained by adding a value near 3×3 pixels to the distance-transformed image (ID), a second intermediate image (IT2) is obtained by performing filter processing for the first intermediate image (IT1) to output a maximum value near the 3×3 pixels, and a third intermediate image (IT3) representing the particle nucleus candidate is obtained by masking the distance-transformed image (ID) using an image obtained by extracting isoplethic points from the first and second intermediate images (IT1, IT2).

According to this invention, the value near the 3×3 pixels is added to the distance-transformed image (ID) to obtain the first intermediate image (IT1), the first intermediate image (IT1) is subjected to filter processing to output the maximum value near the 3×3 pixels to obtain the second intermediate image (IT2), and the distance-transformed image (ID) is masked using an image obtained by extracting isoplethic points from the first and second intermediate images (IT1, IT2) to obtain the third intermediate image (IT3) representing the particle nucleus candidate. The particle nucleus is extracted on the basis of the distance between the particle nucleus candidates in the third intermediate image (IT3) to obtain the particle nucleus image (IC).

According to the fifth invention, in the third invention, a first intermediate image (IT1) is obtained by adding a value near 3×3 pixels to the distance-transformed image (ID), a second intermediate image (IT2) is obtained by performing filter processing for the first intermediate image (IT1) to output a maximum value near the 3×3 pixels, and a third intermediate image (IT3) representing the particle nucleus candidate is obtained by masking the distance-transformed image (ID) using an image obtained by extracting isoplethic points from the first and second intermediate images (IT1, IT2).

According to this invention, the value near the 3×3 pixels is added to the distance-transformed image (ID) to obtain the first intermediate image (IT1), the first intermediate image (IT1) is subjected to filter processing to output the maximum value near the 3×3 pixels to obtain the second intermediate image (IT2), and the distance-transformed image (ID) is masked using an image obtained by extracting isoplethic points from the first and second intermediate images (IT1, IT2) to obtain the third intermediate image (IT3) representing the particle nucleus candidate. The particle nucleus is extracted on the basis of the distance between the particle nucleus candidates in the third intermediate image (IT3) and the separation parameter (PS) to obtain the particle nucleus image (IC).

According to the sixth invention, in the fifth invention, a fourth intermediate image (IT4) is obtained by multiplying the third intermediate image (IT3) by the separation parameter (PS), a fifth intermediate image (IT5) is obtained by performing inverse distance transform for the fourth intermediate image (IT4), a sixth intermediate image (IT6) is obtained by labeling the fifth intermediate image (IT5), and a particle nucleus image (IC) is obtained by masking the sixth intermediate image (IT6) using the third intermediate image (IT3).

According to this invention, the third intermediate image (IT3) is multiplied by the separation parameter (PS) to obtain the fourth intermediate image (IT4), the fourth intermediate image (IT4) is subjected to inverse distance transform to obtain the fifth intermediate image (IT5), the fifth intermediate image (IT5) is labeled to obtain the sixth intermediate image (IT6), and the sixth intermediate image (IT6) is masked using the third intermediate image (IT3) to obtain the particle nucleus image (IC).

According to the seventh invention, in the first to sixth inventions, particle size distribution calculation means (7) for obtaining a size of each particle from the particle-separated image (IS) obtained by the particle expansion means (5) to calculate a particle size distribution is provided. According to the present invention, the size of each particle is obtained from the particle-separated image (IS) to calculate the particle size distribution.

5. BEST MODE OF CARRYING OUT THE INVENTION

Figure 1:
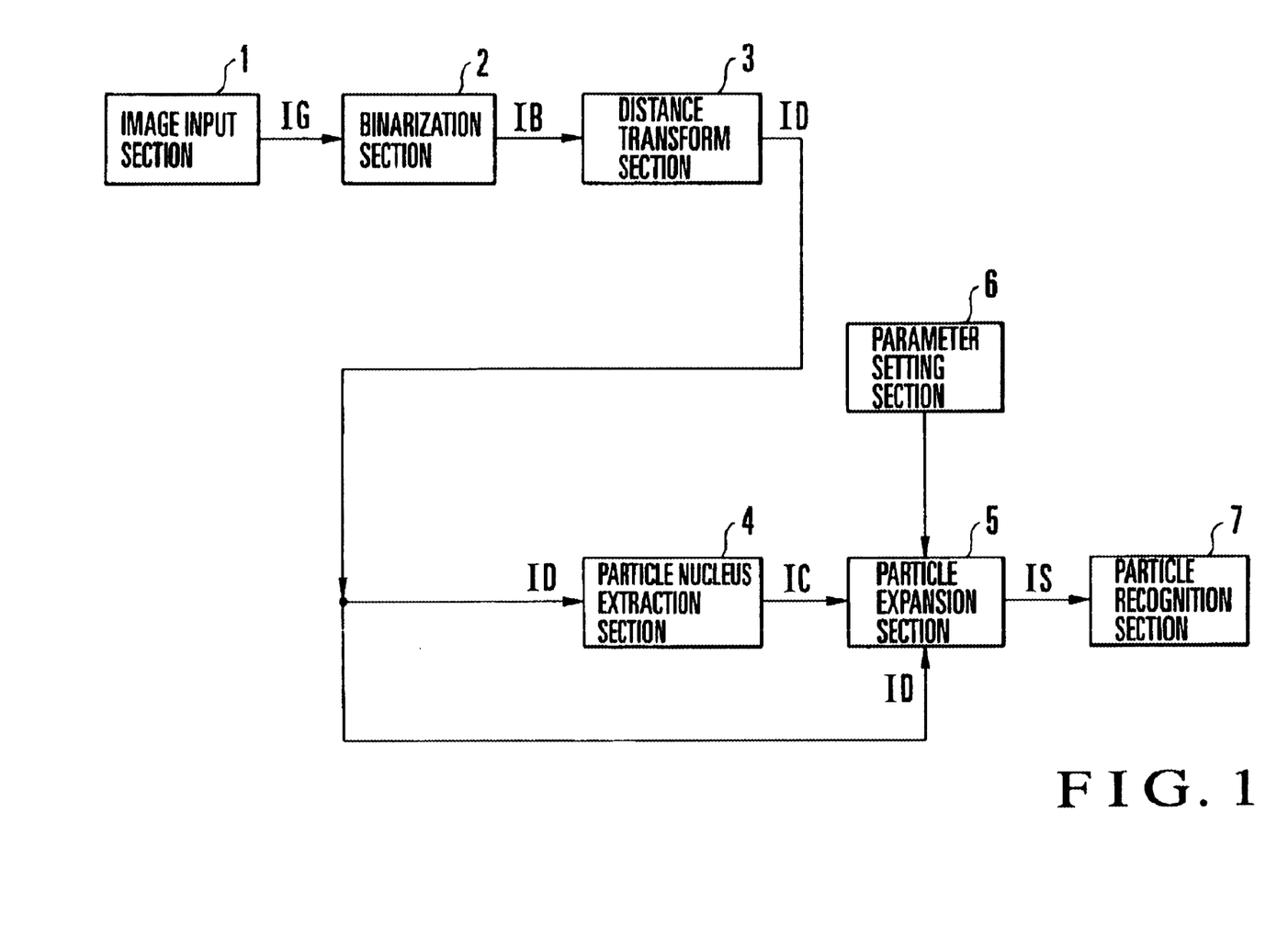
FIG. 1 is a block diagram showing the main part of a particle recognition apparatus according to an embodiment of the present invention.

The present invention will be described below in detail on the basis of an embodiment. FIG. 1 is a block diagram showing the main part of a particle recognition apparatus according to an embodiment of the present invention. Referring to FIG. 1, reference numeral 1 denotes an image input section; 2, a binarization section; 3, a distance transform section; 4, a particle nucleus extraction section; 5, a particle expansion section; 6, a parameter setting section; and 7, a particle recognition section.

The image input section 1 obtains a halftone image IG: IG(x,y) {x,y=0, 1, . . . , N−1} of a photographed to-be-measured particle group having N×N pixels.

Figure 2A:
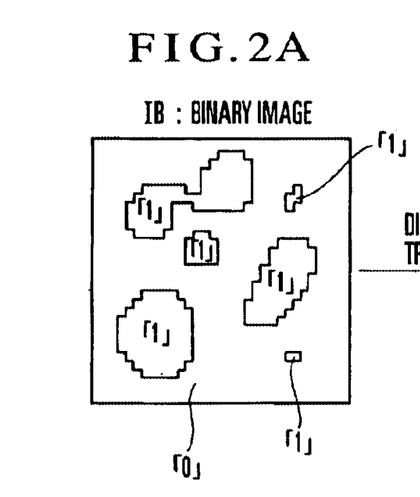
FIG. 2 shows a situation until a particle-separated image is obtained from a binary image in the particle recognition apparatus.

The binarization section 2 obtains a binary image IB: IB(x,y) {x,y=0, 1, . . . , N−1} from the halftone image IG and a predetermined threshold value T using the following equation (FIG. 2(a)).

$$IB(x, y) = \begin{cases} 1 & IG(x, y) \geq T \\ 0 & IG(x, y) < T \end{cases} \quad \text{[Equation 1]}$$

Figure 2B:
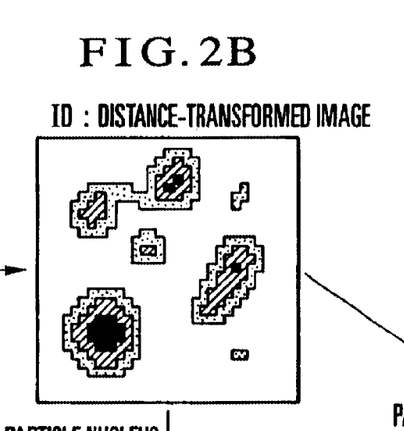

The distance transform section 3 performs distance transform for the binary image IB to obtain a distance-transformed image ID (FIG. 2(b)). In this case, distance transform is transform processing of giving, to a pixel whose value is not "0", the shortest distance to a pixel having a value "0" as a value. Actually, after the image IB is copied to the image ID, processing represented by the following equation is performed twice by scanning.

$$ID(x,y) = \min(ID(a,b)) \ \{a = x-1 \text{ to } x+1, b = y-1 \text{ to } y+1\} + 1$$

Figure 2C:
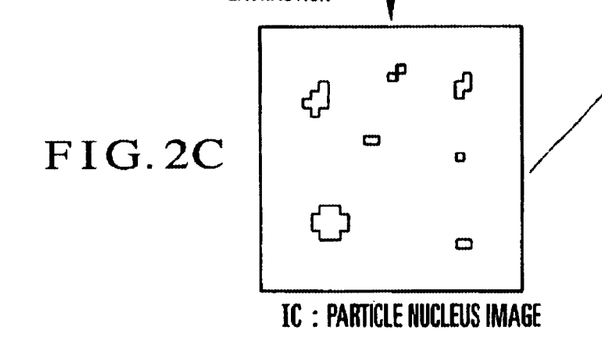

The particle nucleus extraction section 4 obtains particle nucleus candidates from the distance-transformed image ID and extracts a particle nucleus on the basis of the distance between the particle nucleus candidates and a separation parameter PS, thereby obtaining a particle nucleus image IC:

$$IC(x,y) \ \{x,y=0, 1, \ldots, N-1\} \ (\text{FIG. 2}(c)).$$

Figure 2D:
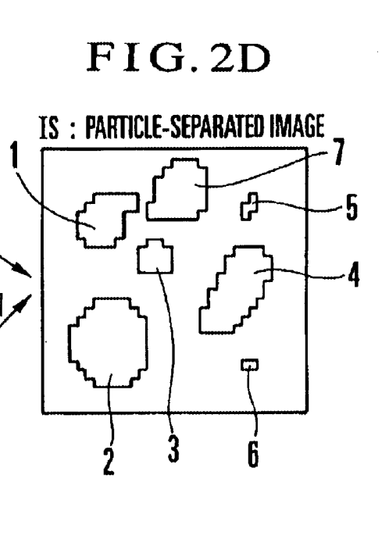

The particle expansion section 5 receives the distance-transformed image ID and particle nucleus image IC and performs particle expansion processing for the particle nucleus in the particle nucleus image IC along the value of distance transform, thereby obtaining a particle-separated image IS: IS(x,y) {x,y=0, 1, . . . , N−1} (FIG. 2(d)).

The parameter setting section 6 sets, for the particle nucleus extraction section 4, the separation parameter PS which defines the degree of extraction (the degree of separation) in particle nucleus extraction processing.

Figure 3:
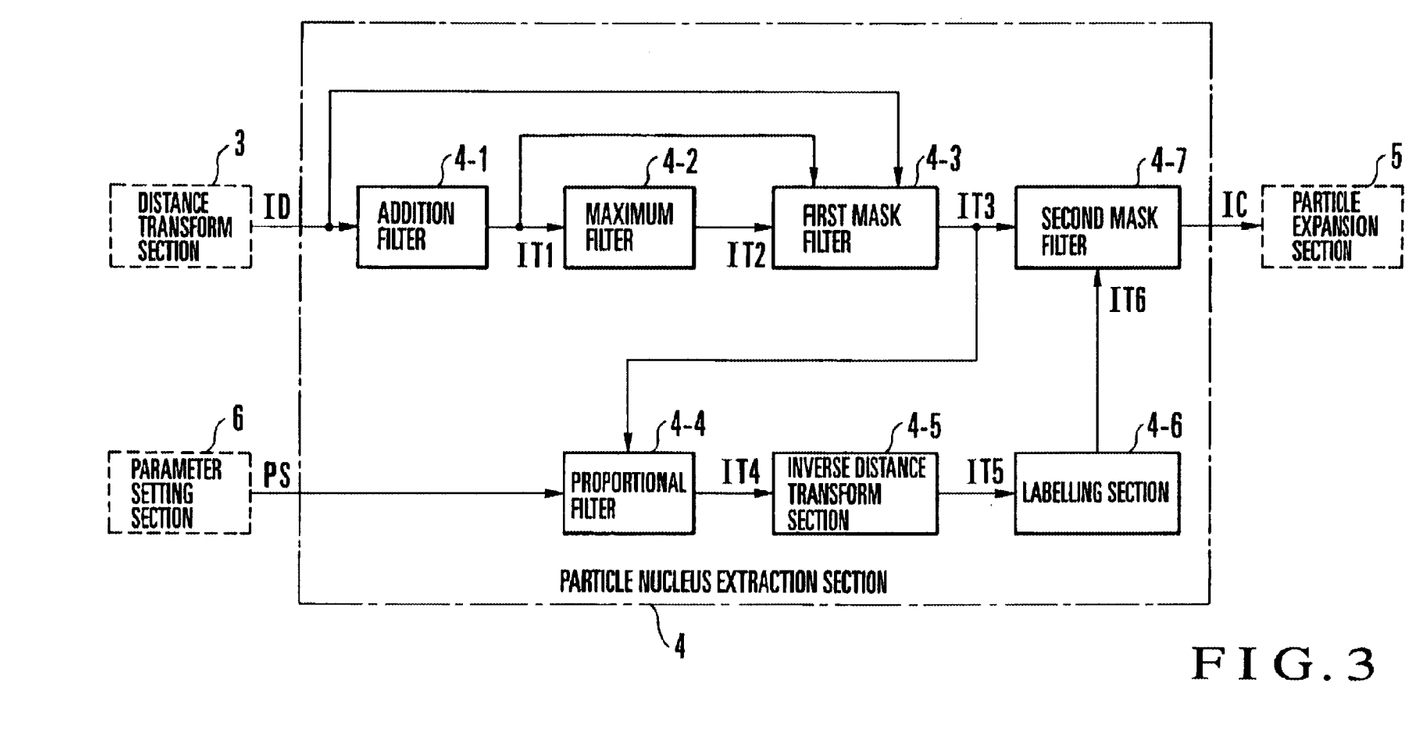
FIG. 3 is a block diagram showing the internal arrangement of a particle nucleus extraction section.

FIG. 3 is a block diagram showing the internal arrangement of the particle nucleus extraction section 4. The particle nucleus extraction section 4 comprises an addition filter 4-1, maximum filter 4-2, first mask filter 4-3, proportional filter 4-4, inverse distance transform section 4-5, labeling section 4-6, and second mask filter 4-7.

Figures 10A, 10B, 10C, 10E, 10F, 10G:
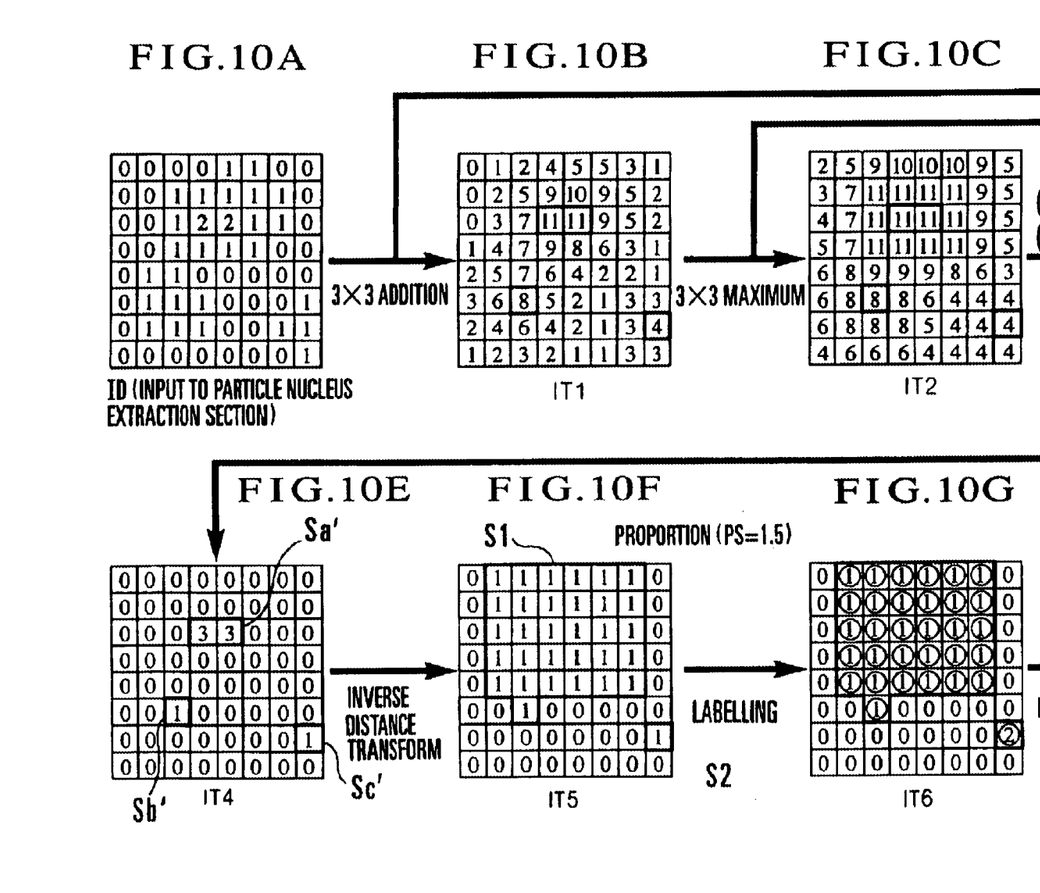
FIG. 10 is a view showing a processing example (8×8) by the particle nucleus extraction section.
Figure 10D:
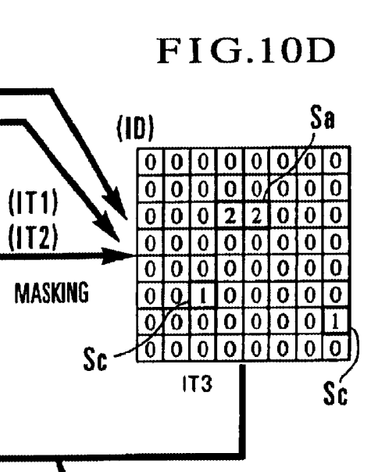
Figure 10H:
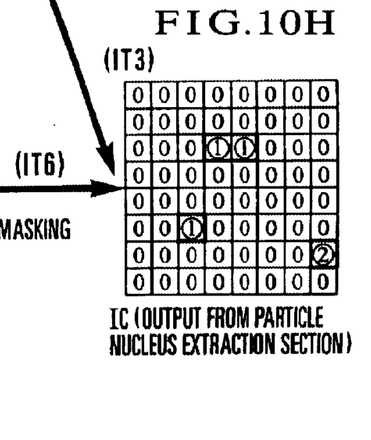

The addition filter 4-1 adds a value near 3×3 pixels to the distance-transformed image ID from the distance transform section 3 to obtain an intermediate image IT1: IT1(x,y) {x,y=0, 1, . . . , N−1} (FIG. 10(b)).

$$IT1(x, y) = \sum_{a=x-1}^{x+1} \sum_{b=y-1}^{y+1} ID(a, b) \quad \text{[Equation 2]}$$

The maximum filter 4-2 performs filter processing for the intermediate image IT1 from the addition filter 4-1 to output the maximum value near 3×3pixels, thereby obtaining an intermediate image IT2: IT2 (x,y) {x,y=0, 1, . . . , N−1} (FIG. 10(c)).

$$IT2(x,y) = \max(IT1(a,b)) \ \{a = x-1 \text{ to } x+1, b = y-1 \text{ to } y+1\}$$

The first mask filter 4-3 masks the distance-transformed image ID from the distance transform section 3 using an image obtained by extracting vertices (isoplethic points) from the intermediate images IT1 and IT2, thereby obtaining an intermediate image IT3: IT3 (x,y) {x,y=0, 1, . . . , N−1} representing a particle nucleus candidate (FIG. 10(d)). In this case, referring to FIG. 10(d), a region Sa represented by a pixel value "2" and regions Sb and Sc represented by a pixel value "1" are particle nucleus candidates.

$$IT3(x, y) = \begin{cases} ID(x, y) \leftarrow IT1(x, y) == IT2(x, y) \\ 0 \leftarrow IT1(x, y)! = IT2(x, y) \end{cases} \quad \text{[Equation 3]}$$

In equations in this specification, "==" represents that the left-hand member and right-hand member equal, "!=" represents that the left-hand member and right-hand member do not equal, and "=" represents a substitution of the value of the right-hand member into the variable of the left-hand member.

The proportional filter 4-4 multiplies the intermediate image IT3 by the separation parameter PS from the parameter setting section 6 to obtain an intermediate image IT4: IT4 (x,y) {x,y =0, 1, . . . , N–1} (FIG. 10(*e*)).

$$IT4\ (x, y) = PS \times IT3\ (x, y)$$

The inverse distance transform section 4-5 performs processing represented by the following equation for the intermediate image IT4 twice by scanning to perform inverse distance transform processing, thereby obtaining an intermediate image IT5: IT5(x,y) {x,y=0, 1, . . . , N–1} (FIG. 10(*f*)).

$$IT5(x, y) = \begin{cases} \max(IT4(a, b)) - 1 \leftarrow \max(IT4(a, b)) > 1 \\ 0 \leftarrow \max(IT4(a, b) \le 1 \end{cases} \quad \text{[Equation 4]}$$

$$(\because a = x - 1\ \text{to}\ x + 1, b = y - 1\ \text{to}\ y + 1)$$

The labeling section 4-6 labels pixels whose values are not "0" in the intermediate image IT5 to obtain an intermediate image IT6: IT6 (x,y) {x,y=0, 1, . . . , N–1} (FIG. 10(*g*)). In this case, referring to FIG. 10(*g*), label ① is given to an inverse distance transform region S1 of a region Sa' represented by a pixel value "3" in FIG. 10(*e*) and a region Sb' close to the region Sa', which is represented by a pixel value "1",and label ② is given to an inverse distance transform region S2 of a region Sc' at a position separated from the region Sa' in FIG. 10(*e*), which is represented by a pixel value "1".

The second mask filter 4-7 masks the intermediate image IT6 using the intermediate image IT6 to obtain the particle nucleus image IC: IC(x,y) {x,y=0, 1, . . . , N–1} (FIG. 10(*h*)). In this case, referring to FIG. 10(*h*), the particle nucleus candidates Sa and Sb in FIG. 10(*d*) are extracted as one particle nucleus represented by label ①, and the particle nucleus candidate Sc is extracted as one particle nucleus represented by label ②.

$$IC(x, y) = \begin{cases} IT6(x, y) \leftarrow IT3(x, y) == 0 \\ 0 \leftarrow IT3(x, y)! = 0 \end{cases} \quad \text{[Equation 5]}$$

Figure 4:
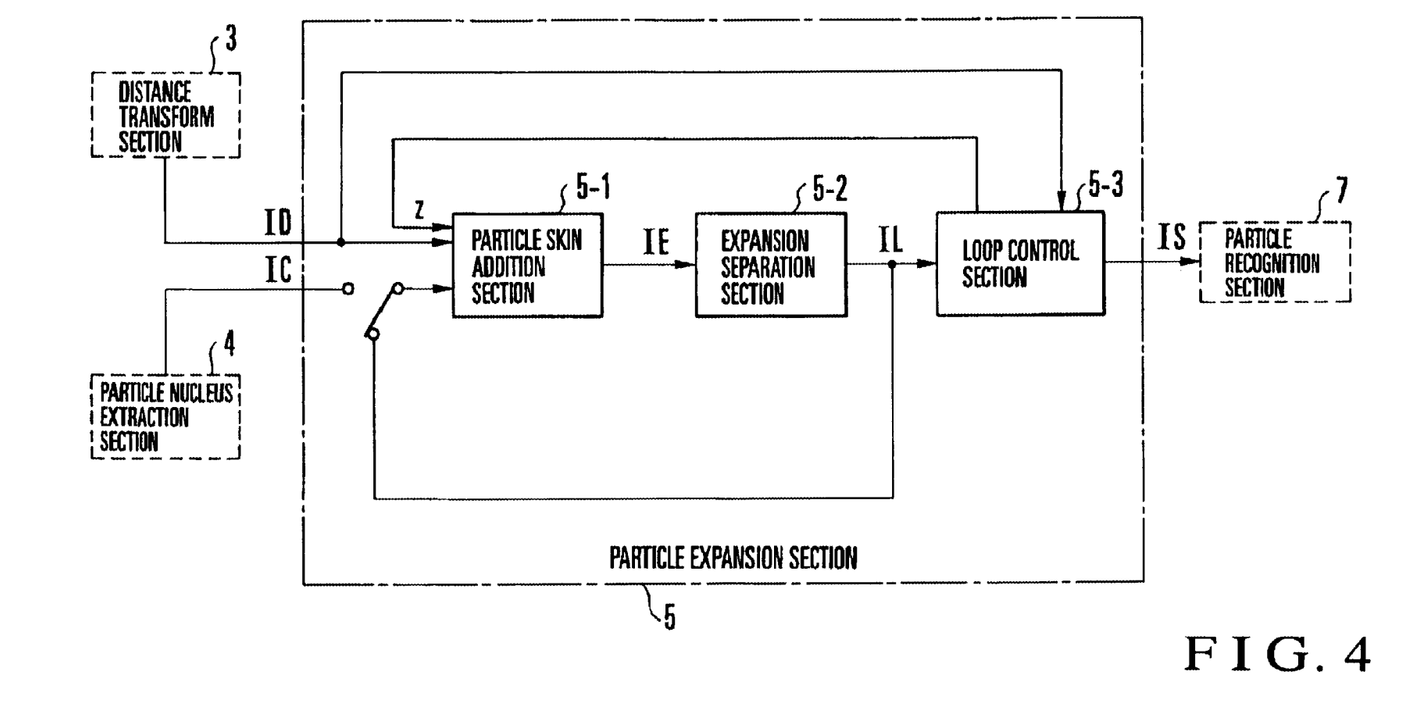
FIG. 4 is a block diagram showing the internal arrangement of a particle expansion section.

FIG. 4 is a block diagram showing the internal arrangement of the particle expansion section 5. The particle expansion section 5 has a particle skin addition section 5-1, expansion separation section 5-2, and loop control section 5-3.

The particle skin addition section 5-1 obtains the distance-transformed image ID from the distance transform section 3 upon receiving a loop count z from the loop control section 5-3. In addition, the particle skin addition section 5-1 obtains the particle nucleus image IC from the particle nucleus extraction section 4 when the value z is the maximum value of distance transform, and otherwise, obtains an intermediate separated image IL from the expansion separation section 5-2, and adds a portion having the value z in the distance-transformed image ID to the particle nucleus image IC or intermediate separated image IL, thereby generating a particle skin image IE.

$$IE(x, y) = \begin{cases} 1 \leftarrow ID(x, y) == k \\ IC(x, y) \leftarrow (ID(x, y)! = k)\ \&(k == \max(ID)) \\ IL(x, y) \leftarrow (ID(x, y)! = k)\ \&(k! = \max(ID)) \end{cases} \quad \text{[Equation 6]}$$

The expansion separation section 5-2 performs the following processing for the particle skin image IE twice by scanning to attach a particle label to a particle skin and expands the particle to generate the intermediate separated image IL. Expansion separation is performed in the following way.

(1): The particle skin image IE is copied to prepare the intermediate separated image IL.
(2): The portion corresponding to IL(x,y)!=1 is kept unchanged.
(3): When IL(x,y)==1, and a value "–1" is present near 3×3 pixels, IL (x,y)=–1.
(4): When IL(x,y)==1, and one kind of label value (integer of 2 or more) is present near 3×3 pixels, the label value is given to IL (x,y).
(5): When IL (x,y)==1, and two or more kinds of label values are present near 3×3 pixels, IL (x,y)=–1.

The loop control section 5-3 is a control section for controlling a loop, which initializes the loop count z by the maximum value of distance transform. Every time the intermediate separated image IL is received from the expansion separation section 5-2, and when z is not 0, the value z is decremented by one and input to the particle skin addition section 5-1, thereby continuing the loop. When z is 0, the particle-separated image IS: IS(x,y) {x,y =0, 1, . . . , N–1} is generated from IE (x,y) and output to the particle recognition section 7, thereby ending the loop.

The particle recognition section 7 receives the particle-separated image IS from the particle expansion section 5 and recognizes each label as one particle.

$$IS(x, y) = \begin{cases} 0 \leftarrow IE(x, y) == -1 \\ IE(x, y) \leftarrow IE(x, y)\ != -1 \end{cases} \quad \text{[Equation 7]}$$

According to this particle recognition apparatus, when particles are separated from the halftone image of a particle group to be measured, and even when a plurality of particles are binarized in contact in the binary image, the particles can be recognized as independent particles. Additionally, even when a particle largely deforms, it can be recognized as one particle without any erroneous separation. In this case, when the appropriate separation parameter PS is set on the basis of the overlap characteristics of particles to be measured or a variation in image input accuracy and measurement environment, accurate particle recognition can be performed. That is, the degree of extraction of particle nuclei (the degree of separation of particles) can be adjusted by adjusting the separation parameter PS, so accurate particle recognition is enabled. Hence, even when the particle image is unclear, the particles can be more accurately separated using this particle recognition apparatus, and the particle recognition accuracy increases. In addition, since particle expansion is performed for extracted particle nuclei along the value of distance transform, the particles can be separated while minimizing deformation of the original particle shapes, and more accurate particle recognition is enabled.

In this particle recognition apparatus, first, distance transform is performed. After particle nuclei are extracted, the particle nuclei are expanded a plurality of number of times by repetitive processing, thereby obtaining the final separated image. In prior art 2, the calculation amount required for repetitive processing of one cycle is enormous because processing such as degeneration, labeling, exclusive expansion, OR, and AND are performed every cycle of repetitive processing. However, the particle recognition apparatus of this embodiment only expands particle nuclei every cycle of repetitive processing. For this reason, the calculation amount is much smaller than that of prior art 2. As a result, the calculation amount of the entire processing is smaller than that of prior art 2.

The effect of the particle recognition apparatus of this embodiment was verified by simulation. Two kinds of images were prepared as particle images.

Figure 5A:
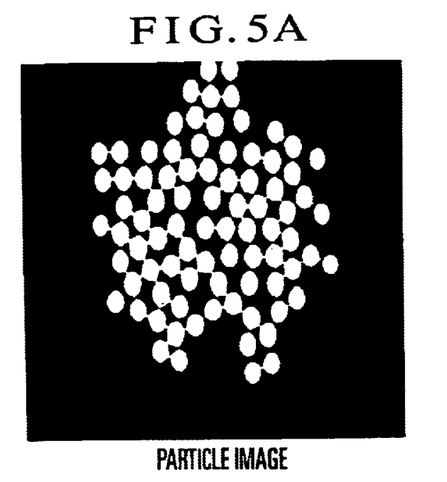
FIG. 5(a) is a photograph showing the particle image (binary image) of a 6-mm spherical particle group, which is displayed on a display.
Figure 5B:
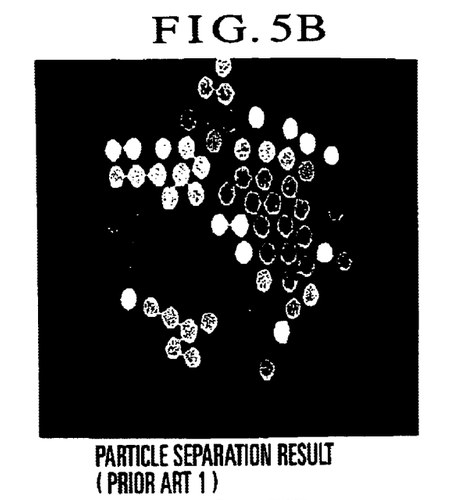
FIG. 5(b) is a photograph showing the particle separation result by the method of prior art 1, which is displayed on the display.
Figure 5C:
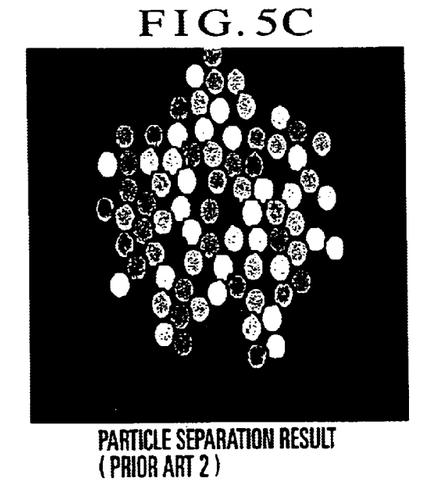
FIG. 5(c) is a photograph showing the particle separation result by the method of prior art 2, which is displayed on the display.
Figure 5D:
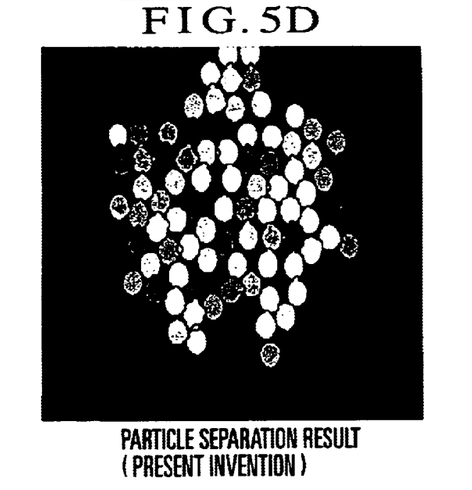
FIG. 5(d) is a photograph showing the particle separation result by a method of the present invention, which is displayed on the display.

First, a 6-mm spherical particle group was photographed and binarized to obtain a particle image. The particle were recognized by the method of prior art 1, the method of prior art 2, and the method of the present invention. The particle recognition results and times required for processing were compared. FIGS. 5(a) to 5(d) show the comparison results. FIG. 5(a) shows the particle image (binary image). FIG. 5(b) shows the particle recognition result by the method of prior art 1. FIG. 5(c) shows the particle recognition result by the method of prior art 2. FIG. 5(d) shows the particle recognition apparatus result by the method of the present invention.

These results reveal the following facts. The method of prior art 1 allows high-speed processing. However, when a plurality of particles are binarized in contact, the plurality of particles in contact are recognized as one particle.

Figure 6:
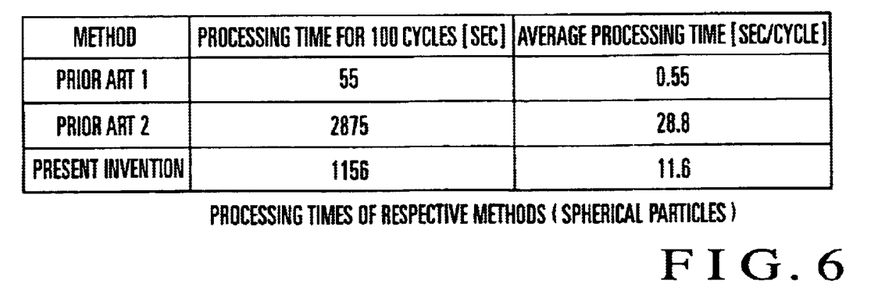
FIG. 6 is a view showing the processing time of each method.

In the method of prior art 2, even when a plurality of particles are binarized in contact, they are recognized as independent particles. The particles can be accurately recognized. However, as shown in FIG. 6, since the calculation amount is large, and processing takes a long time, this method can hardly be adapted to an application purpose with strict restriction on time.

In the method of the present invention, even when a plurality of particles are binarized in contact, they are recognized as independent particles. In addition, the calculation amount is reduced, and it becomes ½ or less that of prior art 2.

Figure 7A:
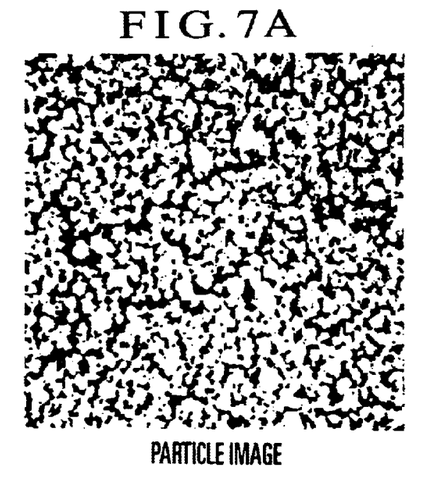
FIG. 7(a) is a photograph showing the particle image (binary image) of a fertilizer on a belt conveyor, which is displayed on a display.
Figure 7B:
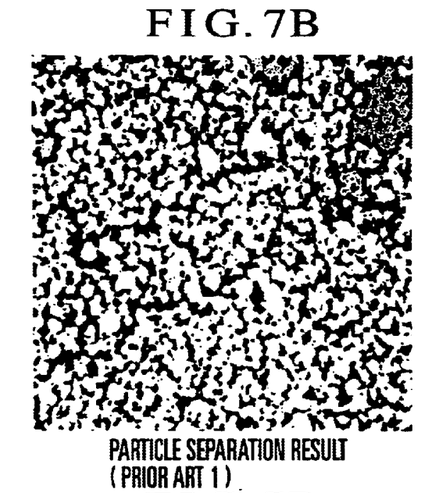
FIG. 7(b) is a photograph showing the particle separation result by the method of prior art 1, which is displayed on the display.
Figure 7C:
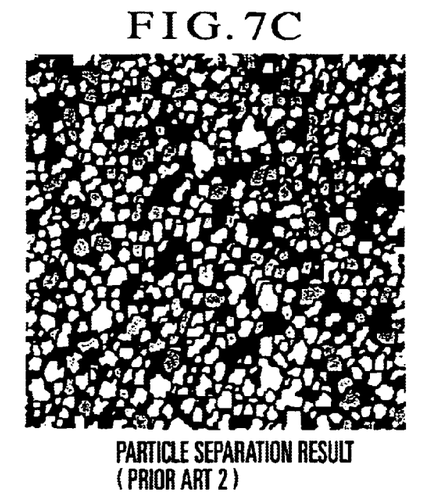
FIG. 7(c) is a photograph showing the particle separation result by the method of prior art 2, which is displayed on the display.
Figure 7D:
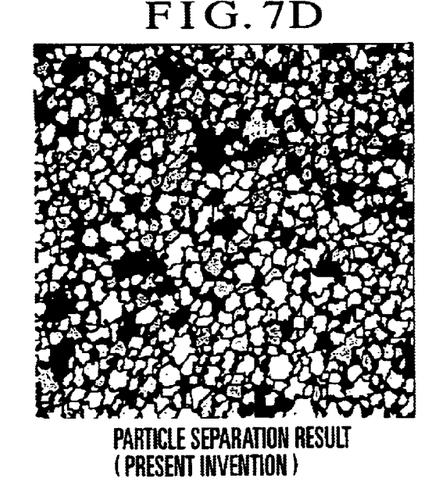
FIG. 7(d) is a photograph showing the particle separation result by a method of the present invention, which is displayed on the display.
Figure 8:
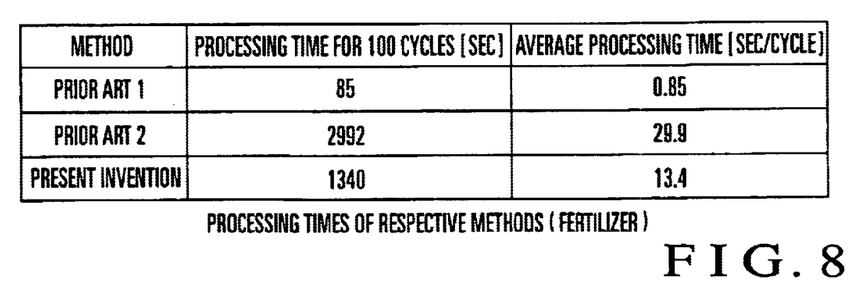
FIG. 8 is a view showing the processing time of each method.

Next, a fertilizer on a belt conveyor was photographed and binarized to obtain a particle image. The particles were recognized by the method of prior art 1, the method of prior art 2, and the method of the present invention. The particle recognition results and times required for processing were compared. FIGS. 7(a) to 7(d) show the comparison results. FIG. 7(a) shows the particle image (binary image). FIG. 7(b) shows the particle recognition result by the method of prior art 1. FIG. 7(c) shows the particle recognition result by the method of prior art 2. FIG. 7(d) shows the particle recognition apparatus result by the method of the present invention.

These results reveal the following facts. In the method of prior art 1, the particle image has particles already binarized in contact. For this reason, a plurality of particles in contact are recognized as one particle, so no correct particle recognition result is obtained.

In the method of prior art 2, separation is performed for a portion where a plurality of particles are binarized in contact. However, since the particles are separated using exclusive expansion, the shape of a separated particle is considerably different from the original shape of the particle image. Additionally, in the method of prior art 2, the calculation amount is large, resulting in a long processing time.

In the method of the present invention, expansion separation for particles of a portion where a plurality of particles are binarized in contact is performed along the value of distance transform. For this reason, the deformation between the shape of a separated particle and the original shape of the particle image is small. This suggests that particle separation faithful to the original image is performed. As a consequence, particles can be accurately recognized. In addition, the calculation amount is decreased, and it becomes ½ or less that of prior art 2.

As is apparent from these results, the method of the present invention allows separation of a particle with a shape closer to the original particle image even when a plurality of particles are in contact. For this reason, a more accurate particle recognition result can be obtained as compared to prior art 1 or prior art 2.

Since the total calculation amount is decreased by decreasing the calculation amount of one cycle of repetitive processing, the required calculation amount is smaller than that of the method of prior art 2. Even when the calculation amount poses a problem in the method of prior art 2, the problem may be solved by introducing the method of the present invention.

Hence, when the method of the present invention is introduced to a target plant such as a chemical plant to perform particle recognition, and the particle size distribution is calculated by obtaining the size of each particle from the resultant particle-separated image, accurate particle size distribution measurement can be performed even when no clear particle image is obtained due to poor environment. In addition, particle size distribution measurement can be performed in a processing time not to impede continuous control of the plant. That is, particle size distribution measurement suitable for continuous operation control of the plant can be performed in terms of systematic performance including the accuracy and processing time. Hence, this method can be applied to a plant where prior art 2 cannot be used. Consequently, the efficiency of control and operation of the plant can be increased, and cost of plant operation can be reduced.

Figure 9:
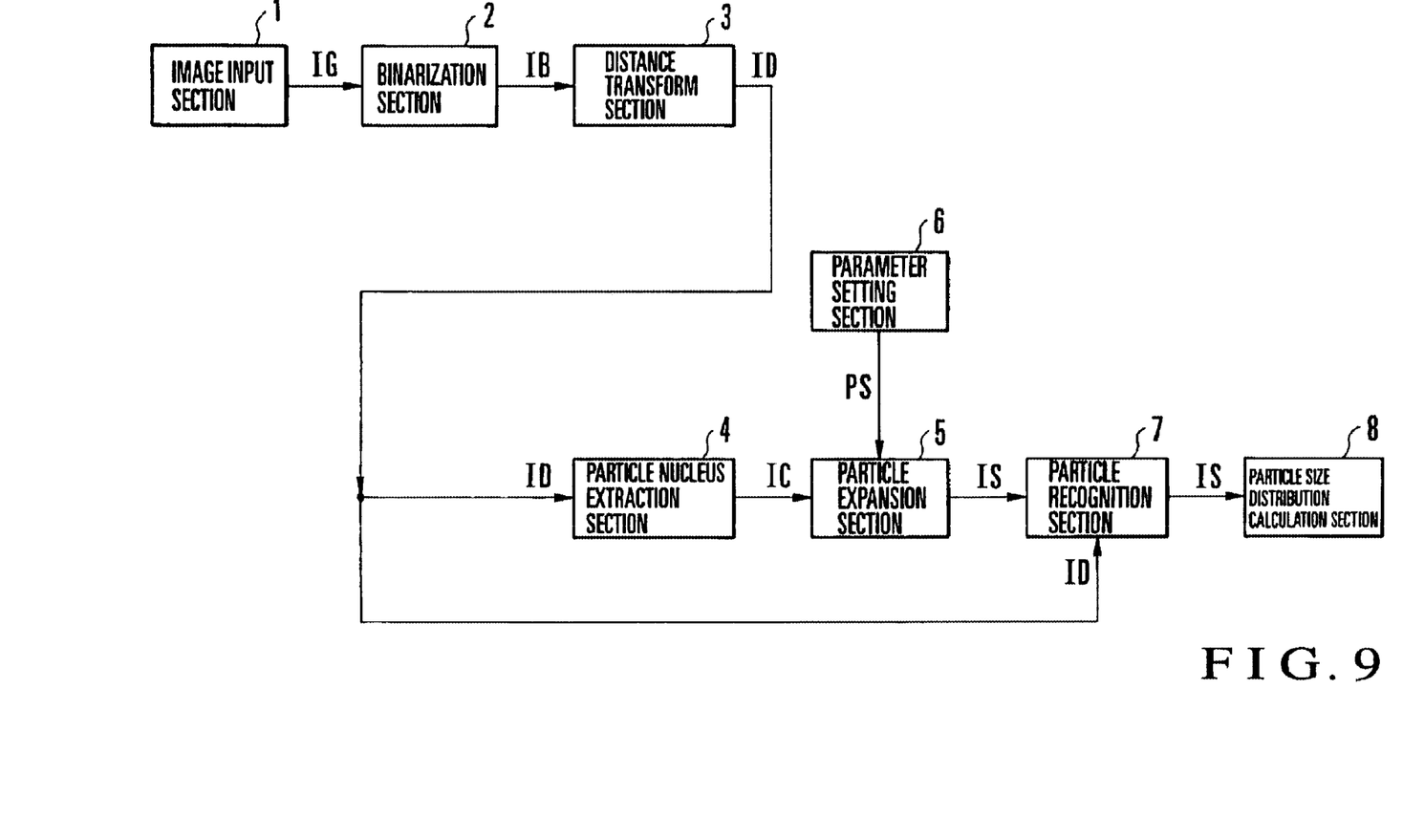
FIG. 9 is a block diagram of a particle recognition apparatus in which a particle size distribution calculation section is added to the arrangement shown in FIG. 1.

FIG. 9 is a block diagram of a particle recognition apparatus added with a particle size distribution calculation section 8. The particle size distribution calculation section 8 obtains a diameter corresponding to a circle from the area of each particle on the basis of the particle-separated image IS to obtain the diameter of the particle, converts the diameter to a weight ratio, and collects weight ratios, thereby obtaining a particle size distribution.

As has been described above, according to the present invention, in the first invention, a halftone image of a particle group to be measured is binarized into a binary image, and the binary image is subjected to distance transform to obtain a distance-transformed image. This distance-transformed image is subjected to particle nucleus extraction processing to obtain a particle nucleus image. The particle nucleus image and distance-transformed image are subjected to particle expansion processing to obtain a particle-separated image. The particles can be recognized at a high speed and high accuracy. More specifically, particles overlapping each other can be separated, the separation accuracy is higher than that of prior art 1, the processing load is lighter than that of prior art 2, and the particles can be recognized at a high speed and high accuracy. Hence, particle recognition suitable for continuous operation control of a plant can be performed in terms of systematic performance including the accuracy and processing time.

In the second invention, since, in the first invention, particle nucleus candidates are obtained from the distance-transformed image, and particle nuclei are extracted on the basis of the particle nucleus candidates, particle nucleus candidates close to each other are regarded as one particle nucleus, thereby increasing the particle nucleus extraction accuracy.

In the third invention, since, in the first invention, the parameter setting means for setting the separation parameter that defines the degree of extraction of particle nuclei in particle nucleus extraction processing is provided, particle nucleus candidates are obtained from the distance-transformed image, and particle nuclei are extracted on the basis of the distance between the particle nucleus candidates and separation parameter, particle recognition suitable for an object to be measured can be performed by setting an appropriate separation parameter in accordance with the overlap characteristics of particles to be measured or a variation in image input accuracy and measurement environment.

In the fourth invention, since, in the second invention, the first intermediate image is obtained by adding the value near 3×3 pixels to the distance-transformed image, the second intermediate image is obtained by performing filter processing for the first intermediate image to output the maximum value near the 3×3 pixels, and the third intermediate image representing a particle nucleus candidate is obtained by masking the distance-transformed image using an image obtained by extracting isoplethic points from the first and second intermediate images, the particle nucleus candidates can be reliably detected, and the particle recognition accuracy is improved.

In the fifth invention, since, in the third invention, the first intermediate image is obtained by adding the value near 3×3 pixels to the distance-transformed image, the second intermediate image is obtained by performing filter processing for the first intermediate image to output the maximum value near the 3×3 pixels, and the third intermediate image representing a particle nucleus candidate is obtained by masking the distance-transformed image using an image obtained by extracting isoplethic points from the first and second intermediate images, the particle nucleus candidates can be reliably detected, and the particle recognition accuracy is improved.

In the sixth invention, since, in the fifth invention, the fourth intermediate image is obtained by multiplying the third intermediate image by the separation parameter, the fifth intermediate image is obtained by performing inverse distance transform for the fourth intermediate image, the sixth intermediate image is obtained by labeling the fifth intermediate image, and a particle nucleus image is obtained by masking the sixth intermediate image using the third intermediate image, particle recognition suitable for an object to be measured can be performed by setting an appropriate separation parameter in accordance with the overlap characteristics of particles to be measured or a variation in image input accuracy and measurement environment. In addition, the particle nuclei can be extracted at a high accuracy, and the particle recognition accuracy is improved.

In the seventh invention, since in the first to sixth inventions, a particle size distribution calculation means for calculating the particle size distribution by obtaining the size of each particle from the particle-separated image obtained by the particle expansion means is provided, the particle size distribution can be measured at a high speed and high accuracy. More specifically, particles overlapping each other can be separated to measure the particle size distribution, the separation accuracy is higher than that of prior art 1, the processing load is lighter than that of prior art 2, and the particle size distribution can be measured at a high speed and high accuracy. Hence, the method is suitable for continuous operation control of a plant in terms of systematic performance including the accuracy and processing time and can be applied to a plant where prior art 2 cannot be used. Consequently, the efficiency of control and operation of the plant can be increased, and cost of plant operation can be reduced.

What is claimed is:

1. A particle recognition apparatus comprising:

image input means for obtaining a halftone image of a particle group to be measured;

binarization means for binarizing the halftone image obtained by said image input means to obtain a binary image;

distance transform means for performing distance transform for the binary image binarized by said binarization means to obtain a distance-transformed image;

particle nucleus extraction means for performing particle nucleus extraction processing for the distance-transformed image obtained by said distance transform means to obtain a particle nucleus image; and particle expansion means for performing particle expansion processing, from the particle nucleus image obtained by said particle nucleus extraction means, along a value of the distance transform of the distance-transformed image obtained by said distance transform means, to obtain a particle-separated image.

2. A particle recognition apparatus according to claim 1, wherein said particle nucleus extraction means obtains particle nucleus candidates from the distance-transformed image obtained by said distance transform means and extracts a particle nucleus on the basis of the distance between the particle nucleus candidates.

3. A particle recognition apparatus according to claim 1, further comprising:

parameter setting means for setting a separation parameter that defines a degree of extraction of the particle nucleus in the particle nucleus extraction processing, and said particle nucleus extraction means obtains particle nucleus candidates from the distance-transformed image obtained by said distance transform means and extracts a particle nucleus on the basis of the distance between the particle nucleus candidates and the separation parameter.

4. A particle recognition apparatus according to claim 2, wherein said particle nucleus extraction means obtains a first intermediate image by adding a value near 3×3 pixels to the distance-transformed image obtained by said distance transform means, obtains a second intermediate image by performing filter processing for the first intermediate image to output a maximum value near the 3×3 pixels, and obtains a third intermediate image representing the particle nucleus candidate by masking the distance-transformed image using an image obtained by extracting isoplethic points from the first and second intermediate images.

5. A particle recognition apparatus according to claim 3, wherein particle nucleus extraction means obtains a first intermediate image by adding a value near 3×3 pixels to the distance-transformed image obtained by said distance transform means, obtains a second intermediate image by performing filter processing for the first intermediate image to output a maximum value near the 3×3 pixels, and obtains a third intermediate image representing the particle nucleus candidate by masking the distance-transformed image using an image obtained by extracting isoplethic points from the first and second intermediate images.

6. A particle recognition apparatus according to claim 5, wherein said particle nucleus extraction means obtains a fourth intermediate image by multiplying the third intermediate image by the separation parameter, obtains a firth intermediate image by performing inverse distance transform for the fourth intermediate image, obtains a sixth intermediate image by labeling the fifth intermediate image, and obtains a particle nucleus image by masking the sixth intermediate image using the third intermediate image.

7. A particle recognition apparatus according to claim 1, further comprising particle size distribution calculation means for obtaining a size of each particle from the particle-separated image obtained by said particle expansion means to calculate a particle size distribution.

8. A particle recognition apparatus comprising:
   an image input section to generate a halftone image of a particle group to be measured;
   a binarization section to binarize the halftone image generated by the image input section to generate a binary image;
   a distance transform section to perform distance transform for the binary image binarized by the binarization section and to generate a distance-transformed image based on the distance transform;
   a particle nucleus extraction section to extract particle nucleus based on the distance-transformed image and to generate a particle nucleus image based on the extracted particle nucleus; and
   a particle expansion section to perform particle expansion processing for the extracted particle nucleus based on a value of the distance transform to generate a particle-separated image.

9. A particle recognition apparatus according to claim 8, wherein the particle nucleus extraction section obtains particle nucleus candidates from the distance-transformed image and extracts a particle nucleus on a basis of a distance between the particle nucleus candidates.

10. A particle recognition apparatus according to claim 8, further comprising:
    a parameter setting section to set a separation parameter that defines a degree of extraction of the particle nucleus in the particle nucleus extraction processing,
    wherein the particle nucleus extraction section obtains particle nucleus candidates from the distance-transformed image and extracts a particle nucleus on a basis of a distance between the particle nucleus candidates and the separation parameter.

11. A particle recognition apparatus according to claim 9, wherein the particle nucleus extraction section obtains a first intermediate image by adding a value near 3×3 pixels to the distance-transformed image, obtains a second intermediate image by performing filter processing for the first intermediate image to output a maximum value near the 3×3 pixels, and obtains a third intermediate image representing the particle nucleus candidate by masking the distance-transformed image using an image obtained by extracting isoplethic points from the first and second intermediate images.

12. A particle recognition apparatus according to claim 10, wherein the particle nucleus extraction section obtains a first intermediate image by adding a value near 3×3 pixels to the distance-transformed image, obtains a second intermediate image by performing filter processing for the first intermediate image to output a maximum value near the 3×3 pixels, and obtains a third intermediate image representing the particle nucleus candidate by masking the distance-transformed image using an image obtained by extracting isoplethic points from the first and second intermediate images.

13. A particle recognition apparatus according to claim 12, wherein the particle nucleus extraction section obtains a fourth intermediate image by multiplying the third intermediate image by the separation parameter, obtains a firth intermediate image by performing inverse distance transform for the fourth intermediate image, obtains a sixth intermediate image by labeling the fifth intermediate image, and obtains a particle nucleus image by masking the sixth intermediate image using the third intermediate image.

14. A particle recognition apparatus according to claim 8, further comprising a particle size distribution calculation section to obtain a size of each particle from the particle-separated image obtained by said particle expansion section to calculate a particle size distribution.

\* \* \* \* \*

UNITED STATES PATENT AND TRADEMARK OFFICE
CERTIFICATE OF CORRECTION

PATENT NO. : 6,728,405 B1
DATED : April 27, 2004
INVENTOR(S) : Kazato et al.

It is certified that error appears in the above-identified patent and that said Letters Patent is hereby corrected as shown below:

Title page,
Item [54], Title, please delete "PARTICLE RECOGNITION DEVICE" and insert
-- PARTICLE RECOGNITION APPARATUS --.

Signed and Sealed this

Eighth Day of February, 2005

JON W. DUDAS
*Director of the United States Patent and Trademark Office*